United States Patent [19]

Casey et al.

[11] Patent Number: 4,754,070

[45] Date of Patent: Jun. 28, 1988

[54] HYDROGENATION OF METHYLENEDIANILINE TO PRODUCE BIS(PARA-AMINOCYCLOHEXYL)METHANE

[75] Inventors: Jeremiah P. Casey, Emmaus; Michael J. Fasolka, Pennsburg, both of Pa.

[73] Assignee: Air Products and Chemicals, Inc., Allentown, Pa.

[21] Appl. No.: 821,629

[22] Filed: Jan. 23, 1986

[51] Int. Cl.$^4$ .............................................. C07C 65/24
[52] U.S. Cl. ............................ 564/451; 564/452
[58] Field of Search ............................... 564/451, 452

[56] References Cited

U.S. PATENT DOCUMENTS

| | | | |
|---|---|---|---|
| 2,511,028 | 6/1950 | Whitman | 564/451 |
| 2,606,924 | 8/1952 | Whitman | 564/451 |
| 2,606,925 | 8/1952 | Whitman | 564/451 |
| 2,606,928 | 8/1952 | Barkdoll et al. | 564/451 |
| 3,155,724 | 11/1964 | Arthur | 564/451 |
| 3,347,917 | 10/1967 | Arthur | 564/451 |
| 3,591,635 | 7/1971 | Farissey et al. | 564/451 |
| 3,636,108 | 1/1972 | Brake | 564/451 |
| 3,644,522 | 2/1972 | Brake et al. | 564/451 |
| 3,679,746 | 7/1972 | Brake | 564/444 |
| 3,697,449 | 10/1972 | Brake | 252/474 |
| 3,711,550 | 1/1973 | Brake | 564/451 |
| 3,743,677 | 7/1973 | Grosskinsky et al. | 564/451 |
| 3,766,272 | 10/1973 | Brake | 564/444 |
| 3,856,862 | 12/1974 | Chung et al. | 564/451 |
| 4,394,522 | 7/1983 | Allen | 564/451 |
| 4,394,523 | 7/1983 | Allen | 564/451 |
| 4,448,995 | 5/1984 | Allen | 564/451 |

FOREIGN PATENT DOCUMENTS 0066212 12/1982 European Pat. Off. ............ 564/451

*Primary Examiner*—Glennon H. Hollrah
*Assistant Examiner*—John A. Sopp
*Attorney, Agent, or Firm*—Russell L. Brewer; James C. Simmons; William F. Marsh

[57] ABSTRACT

This invention relates to an improved hydrogenation process wherein methylenedianiline is reduced to form bis(para-aminocyclohexyl)methane (PACM). The process contemplates contacting methylenedianiline and hydrogen in the presence of a two component metal catalyst comprising rhodium and ruthenium under mild hydrogenation conditions. Use of the mixed metal catalyst system allows one to obtain a preselected isomer ratio having from about 5–40% by weight, typically 14–28% by weight of the trans,trans- configurational isomer.

8 Claims, No Drawings

HYDROGENATION OF METHYLENEDIANILINE TO PRODUCE BIS(PARA-AMINOCYCLOHEXYL)METHANE

TECHNICAL FIELD

This invention pertains to a process for hydrogenating methylenedianiline to produce a preselected isomer ratio of bis(para-aminocyclohexyl)methane.

BACKGROUND OF THE INVENTION

There is substantial literature in the art with respect to the hydrogenation of methylenedianiline to produce 4,4'-methylenedi(cyclohexylamine), also called bis(para-aminocyclohexyl)methane, and bis(4-aminocyclohexyl)methane hereinto after referred to as PACM. Some of the early work was done by Whitman and Barkdoll, et al. and their work is set forth in a series of U.S. Pat. Nos. e.g., 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80 to 275° C. utilizing a ruthenium catalyst for the hydrogenation. The hydrogenation is carried out under liquid phase conditions and an inert organic solvent is used in the hydrogenation process. Examples of ruthenium catalysts utilized for the hydrogenation process include ruthenium oxides such as ruthenium sesquioxide and ruthenium dioxide; and ruthenium salt.

Brake, et al. continued in the manufacture of PACM by hydrogenating methylenedianiline. They found that if the ruthenium was carried upon a support and the support alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108; 3,644,522; and U.S. Pat. No. 3,697,449. Alkali metal and alkaline earth metal nitrates and sulfates have similarly been shown effective in U.S. 4,448,995 under high pressure (4000 psi) hydrogenation conditions.

U.S. Pat. No. 3,959,374 discloses a process for the preparation of PACM by pretreating a mixed methylenedianiline system with a nickel containing hydrogenation catalyst prior to hydrogenation with ruthenium. The pretreatment was alleged to overcome low yields (52.4%) and long reaction associated with nickel and cobalt. Ruthenium catalysts, although commonly used for hydrogenation, were not suited for hydrogenation of a feed containing impurities, e.g. isomeric impurities. Impurities in the feed allegedly caused a rapid decline in activity and hydrogenation efficiency.

One of the early uses of PACM was for the production of various nylons and these nylons were prepared by reacting PACM with sebacic acid or adipic acid. Nylons of various quality were produced when PACM was reacted with these acids, such quality being affected by the relative concentration of the particular isomers of PACM used in the reaction. The cis,cis(m.p. 60.5–61.9° C.) and especially the cis,trans(m.p. 35.7–36.9° C.) geometric isomers are lower melting than the trans,trans(m.p. 64-65.4° C.) isomer. When reacted with sebacic or adipic acid they, or particularly the even lower melting mixture of isomers, produce a nylon having a cloudy and opaque appearance and infusible whereas if the higher melting isomer; i.e., the trans,-trans-isomer were utilized the nylon would be clear, transparent, and fusible.

U.S. Pat. Nos. 3,347,917; 3,711,550; 3,679,746; 3,155,724; 3,766,272 and British Pat. No. 1,122,609 disclose various-isomerization processes and hydrogenation processes to produce PACM containing high trans,trans-isomer content; i.e. an isomer content near equilibrium typically 50% trans,trans-, 43% cis,trans and 7% cis,cis-. As in the early work ruthenium catalysts were used to effect isomerization. This product was often called PACM-50.

Another use of PACM was in the preparation of an aliphatic isocyanate suited for forming light stable urethane coatings and lacquers. This diisocyanate was obtained from a secondary product low in trans,transisomer. This product was obtained upon separation of the more desirable trans,trans- isomer from the reaction product mixture of isomers produced by the hydrogenation of methylenedianiline in the presence of ruthenium. The secondary or residual product contained approximately 20% of the trans,trans- isomer and was referred to as PACM-20. PACM-20 exhibited utility in the manufacture of liquid isocyanates. 4,4'-Methylenedi(cyclohexylisocyanate) ($H_{12}MDI$) produced upon phosgenation of the methylenedi(cyclohexylamine) was a liquid diisocyanate stable to storage at room temperature; e.g., from 20 to 25° C. In contrast PACM-50, which contained approximately 50% trans,trans- isomer, resulted in the production of $H_{12}MDI$ which was a solid at room temperature. Accordingly, for purposes of isocyanate production and further utilization in the manufacture of polyurethane formulations, PACM-20 was preferred to PACM-50 for the synthesis of the aliphatic diisocyanate.

With the growth of the polyurethane industry it has become desirable to produce substantial quantities of PACM-20 in preference to PACM-50. Allen in U.S. Pat. No. 4,394,522 and U.S. Pat. No. 4,394,523 discloses processes for producing PACM which contains the trans,trans- isomer in relatively narrow amounts e.g. from 15 to 40% and preferably less than 40% by weight. The synthesis of PACM containing less than 40% by weight of the trans,trans- isomer is achieved by carrying out the hydrogenation of MDA in the presence of unsupported ruthenium dioxide at pressures of at least 2500 psia or in the presence of ruthenium on alumina under pressures of at least 500 psia and preferably from 1500 to 4000 psia in the presence of an aliphatic alcohol and ammonia. Major disadvantages of these processes are the equipment require.d for high pressures and, as cited in U.S. Pat. No. 3,743,677, the inability to maintain high yields of such reactions when they are carried out on a commercial scale due to inadequate temperature control.

Other catalysts have been utilized for the hydrogenation of methylenedianiline and examples are shown in U.S. Pat. No. 3,591,635 and U.S. Pat. No. 3,856,862. Both disclose the use of a rhodium component as a catalytic material and each require the use of an aliphatic alcohol as a solvent. The rhodium is alkali moderated using ammonium hydroxide as a pretreatment or by carrying out the reaction in the presence of ammonia. Also, in European application 66,212 rhodium on alumina in butyl ether is disclosed to obtain 15-40% trans,trans- isomer ratio contents, but again the pressures are high (4000 psi) and the reaction times short, leading to difficult reaction product control.

SUMMARY OF THE INVENTION

This invention relates to an improved process for producing 4,4'-methylenedi(cyclohexylamine) (PACM) by the catalytic hydrogenatipn of 4,4'-methylenedianiline. The improvement in the hydrogenation process to produce PACM having a trans,trans- isomer content of less than about 40% and to a low of about 5% by weight is achieved by using a mixture of catalytic components comprising rhodium and ruthenium wherein the weight ratio of rhodium to ruthenium, calculated on metal content, is from 2 to 12:1. In a preferred case at least the rhodium component is alkali moderated.

There are several advantages associated with this process. These include:

an ability to produce a hydrogenated methylenedianiline having a trans,trans- isomer concentration of 40% and less;

an ability to effect hydrogenation of methylenedianiline to form PACM at relatively low pressures e.g. 1500 psig and lower;

an ability to utilize an impure methylenedianiline, i.e. one containing oligomers as a reactant and yet obtain PACM in high selectivity;

an ability to obtain a reaction product which is substantially free of by-product oligomers and other heavies;

an ability to produce preselectad isomer ratios of PACM within a 5-40% weight range and generally in the 14-28% and preferably about 17-24% trans,trans- isomer range; and an ability to use the catalyst for continued periods of time with only modest maintenance or regeneration techniques.

DETAILED DESCRIPTION OF THE INVENTION

As is known three isomers are produced by the conventional hydrogenation of bis(4-aminophenyl)methane and these configurational isomers are represented by the formulas:

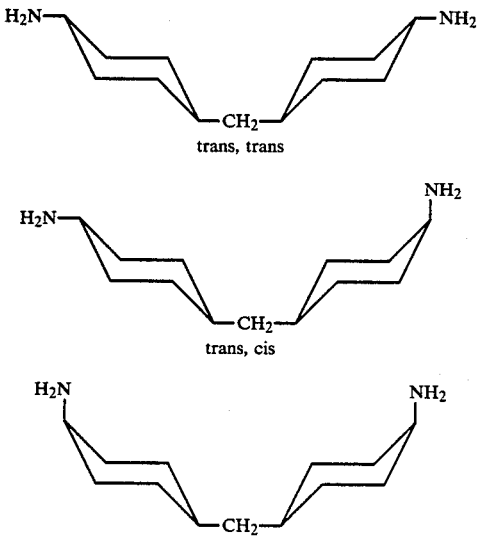

-continued cis, cis

Each isomer has a different characteristic and these characteristics influence the type of products produced therefrom. Nylon and isocyanates which can be produced from the hydrogenated product are examples of products influenced by the particular isomer used in the synthesis.

By the practice of this invention, one is able to selectively produce a hydrogenation reaction product containing isomers in a ratio other than the equilibrium ratio of approximately 50% trans,trans-/43%, cis,trans-/7% cis,cis-, actually 54.5%, 38.5% and 7%. As with conventional processes the hydrogenation process is carried out under liquid phase conditions, such liquid phase conditions being maintained typically by carrying out the hydrogenation in the presence of a solvent. Although as reported in the art, it is possible to produce the reaction product in the absence of a solvent, the processing is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained so that the water concentration is less than 0.5% by weight. Water, when present in the system, tends to increase the amount of byproduct alcohols and heavy condensation products during the hydrogenation process and tends to deactivate the catalyst system.

When a solvent is used, it can be used in concentrations as low as 0% by weight based upon the methylenedianiline (MDA) introduced into the reaction and typically the solvent is used at levels from about 75 to about 200% by weight of the starting compound. Under some circumstances solvent amounts as high as 1000 to 2000% based upon the weight of the MDA are used.

The hydrogenation is carried out principally in a batch process although it is possible to operate the plant continuously. Temperatures used for the hydrogenation process range from about 130° to 220° C. with preferred temperatures of from about 170° to 195° C. When the temperature exceeds about 190° C., higher pressures and shorter reaction times are required to reduce the amount of trans,trans- isomer produced. This is particularly true where the content of the trans,trans- isomer is targeted in a range from about 17 to 24% by weight.

In contrast to the prior art hydrogenation processes, hydrogen partial pressures can range from about 500 to 2500 psig and can be as low as from about 700 to 1500 psig, which may be preferred for lower equipment operating costs. When the pressure is raised toward the upper end of the operating range, reaction temperatures may be increased and greater concentrations of the trans, trans- isomer are produced. However, even at those pressures, the trans,trans- isomer is less than the equilibrium concentration and generally less than 30% by weight.

The ability to hydrogenate methylenedianiline at low hydrogen partial pressures and to limit formation of the trans,trans- isomer content is achieved by the utilization of a specific catalyst system. In contrast to the prior art the catalyst utilized in the hydrogenation process comprises a mixed metal catalyst system, the metals being rhodium and ruthenium. This catalyst system permits kinetic control of the reaction at low pressures, the ease of reaction of the mixed metal system being unexpectedly superior to the ease of reaction noted with either catalyst individually. The catalysts can be prepared separately and added to the reactor individually or they may be physically admixed or they may be combined and used as a single component. To simplify preparation and processing it is preferred to admix the two catalysts and incorporate them into the reaction medium as an admixture.

The catalysts are combined, based upon their weights as metal, in a ratio of about 2 to 12 parts rhodium per part of ruthenium, preferably 4 to 8 parts rhodium per part ruthenium. When the ratio of rhodium to ruthenium, as metal, approaches the lower limit of the range the level of trans,trans- isomer increases. As the concentration of rhodium increases vis-a-vis ruthenium the activity of the catalyst system increases and therefore lower temperatures or catalyst concentrations may be satisfactory.

The catalysts used and practiced in this invention generally are supported upon an inert carrier and representative carriers include carbon, calcium carbonate, rare earth oxides, such as cerium, praseodymium, or lanthanum; rare earth oxides or carbonates; alumina; barium sulfate; kieselguhr; pumice; titania; diatomaceous earth; and alkaline earth components such as calcium sulfate, calcium oxide, barium oxide, and barium sulfate. Preferred support materials are alumina and carbon.

To maintain high activity of the catalyst system in the hydrogenation process it is proposed that at least the rhodium component of the catalyst is alkali moderated. Alkali moderation techniques to produce the catalyst system are well known and the techniques disclosed in U.S. Pat. No. 3,636,108 for the alkali moderation of ruthenium can be utilized for the production of rhodium. Such method is incorporated by reference. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, moderation of the catalyst is done prior to reduction of the catalyst with aqueous dilute alkali metal hydroxide during or following metal deposition on the chosen support. Alkali moderation can also be accomplished in situ during hydrogenation by including alkali metal hydroxide, alkali metal alkoxide or by the addition of ammonia. For purposes of practicing this invention it is preferred that the catalyst is alkali moderated prior to reduction and maintained in situ with additions of alkali metal hydroxide.

In contrast to many prior art hydrogenation processes alkali moderation of ruthenium is not critical to the production of PACM-20 as it is in the production of PACM-50. For example, if both of the catalytic components are alkali moderated; i.e. the rhodium component and the ruthenium component, the reaction product is essentially the same as the product produced using alkali moderated rhodium as the only alkali moderated component of the catalyst system. As appreciated for all aromatic amine reductions, however, the simple alkali metal compound, lithium hydroxide, is particularly effective in decreasing coupling reactions, suppressing hydrogenolysis and eliminating a strong inhibitory action of ammonia along with the secondary amine.

The progress of a hydrogenation reaction can readily be followed by observing the amount of hydrogen taken up by the reaction mixture and the reaction is terminated when the amount of hydrogen absorbed is equal to that amount necessary to effect complete hydrogenation of the product. In general, the hydrogenation time will range from about 45 to 900 minutes, at modest catalyst levels, e.g., 0.5-2.5% by weight of the MDA, and generally will not exceed 300 minutes. The reaction time can be adjusted to adjust isomer selectivity of the reaction product. Typically, when operating at higher temperatures, a higher amount of trans,trans-configurational isomer is produced and that level of isomer may be reduced by utilizing a shorter reaction time through higher catalyst loading. Generally, longer reaction times and higher temperatures favor the production of the more thermodynamically stable trans,trans- isomer.

The following examples are intended to illustrate various embodiments of the invention and all parts and percentages given are weight parts or weight percents unless otherwise specified.

EXAMPLE 1

A series of hydrogenation processes were carried out in pressure vessels of 300 cc, 1 liter and 1 gallon capacity. The size of the vessel employed was believed to have no effect on the hydrogenation process or product selectivity. Each vessel was equipped with an agitator and temperature control means. The general process used was similar to prior art liquid phase batch processas for producing PACM. More specifically, solvent, catalyst and 4,4'-methylenedianiline (MDA), either pure or in crude form, were charged to the vessel and heated to reaction temperature under hydrogen injected into the vessel to a preselected pressure and the hydrogenation carried out for a preselected time or until hydrogen consumption ceased. At the conclusion of the reaction, the reaction mixture was cooled and filtered free of catalyst. Products were analyzed for isomer content by capillary column GC using either the reaction solvent medium or, after fractionation by distillation, a solution of the distilled product.

Several of the runs carried out in the pressure vessels are reported in Table 1 below. In Table 1 the following abbreviations are used:

REACTANT PBW refers to the weight of MDA in grams, MDA refers to crude MDA and includes from 10-30% by weight of oligomers, typically about 15%;

CAT refers to the type of catalyst employed, e.g., Ru/Al2O3, refers to ruthenium on alumina;

4Rh1RuAl refers to a catalyst system consisting of 4 weight parts rhodium and 1 weight part ruthenium as metal, both being supported on alumina (other numbers may be used to indicate different metal ratios and supports may be used);

CAT pBW refers to the weight in grams of catalyst used in the reaction;

PRESSURE refers to the pressure in psig;

TEMP refers to the temperature in degrees C.;

TIME refers to the reaction time in minutes;

GC CONV refers to conversion of MDA effected as determined by gas chromatography;

GC YIELD refers to integrated area percentage of PACM in the GC-elutable product;

PCT TT, PCT CT and PCT CC refers to the weight percent of the specific isomer listed as converted from GC area percent;
 (a) TT referring to trans,trans-,
 (b) CT referring to cis,trans- and
 (c) CC referring to cis,cis-;

HEAVIES refers to secondary amine condensation products which elute late under the capillary GC conditions chosen (GC area percent);

SOLVENT refers to the type of solvent used in the process with THF referring to tetrahydrofuran;

SOL PBV refers to the volume in milliliters of solvent added to the pressure vessel;

$NH_3$ PBW refers to the weight of ammonia added to the pressure vessel;

NaOH ML refers to the milliliters of 50% aqueous sodium hydroxide added to the pressure vessel during hydrogenation;

LiOH MG refers to the milligrams of lithium hydroxide added to the pressure vessel.

THF refers to tetrahydrofuran;
Diox refers to dioxane;
n $Bu_2O$ refers to n-butyl ether.

TABLE 1

METHYLENEDIANILINE HYDROGENATIONS

| RUN | REACTANT PBW | CAT | CAT PBW | PRESSURE | TEMP °C. | TIME MIN | GC CONV | GC YIELD |
|---|---|---|---|---|---|---|---|---|
| 1 | 50 | $Ru/Al_2O_3$ | 5.0 | 2500 | 180 | 90 | 100 | 91 |
| 2 | 50 | $Ru/Al_2O_3$ | 5.0 | 850 | 180 | 240 | 100 | 99 |
| 3 | 50 | $Ru/Al_2O_3$ | 5.0 | 2500 | 180 | 90 | 100 | 93 |
| 4 | 50 | $Ru/Al_2O_3$ | 5.0 | 2500 | 180 | 120 | 29 | 1 |
| 5 | 50 | $Ru/Al_2O_3$ | 5.0 | 850 | 180 | 120 | 88 | 13 |
| 6 | 50 | $Ru/Al_2O_3$ | 5.0 | 850 | 180 | 300 | 95 | 21 |
| 7 | 50 | $Ru/Al_2O_3$ | 2.5 | 850 | 160 | 255 | 100 | 97 |
| 8 | 50 | $Rh/Al_2O_3$ | 2.5 | 2500 | 180 | 75 | 100 | 98 |
| 9 | 50 | $Rh/Al_2O_3$ | 2.5 | 850 | 195 | 30 | 94 | 14 |
| 10 | 50 | $Rh/Al_2O_3$ | 5.0 | 850 | 160 | 90 | 100 | 96 |
| 11 | 50 | $Rh/Al_2O_3$ | 2.5 | 850 | 125 | 135 | 97 | 58 |
| 12 | 50 | $Rh/Al_2O_3$ | 2.5 | 850 | 160 | 240 | 100 | 99 |
| 13 | 50 | $3Rh_2RuAl$ | 5.0 | 850 | 160 | 75 | 100 | 98 |
| 14 | 50 | $4Rh_1RuAl$ | 5.0 | 850 | 165 | 180 | 100 | 98 |
| 15 | 50 | $4Rh_1RuAl$ | 4.5 | 850 | 165 | 195 | 100 | 98 |
| 16 | 200 | $9Rh_1RuAl$ | 10.0 | 1100 | 160 | 300 | 100 | 99 |
| 17 | 200 | $9Rh_1RuAl$ | 10.0 | 850 | 160 | 300 | 100 | 99 |
| 18 | 200 | $9Rh_3RuAl$ | 12.0 | 850 | 160 | 240 | 100 | 98 |
| 19 | 667 | $10Rh_1RuAl$ | 28.7 | 850 | 185 | 200 | 100 | 99 |
| 20 | 900 | $10Rh_2RuAl$ | 31.3 | 850 | 185 | 170 | 100 | 99 |
| 21 | 1433 | $10Rh_2RuAl$ | 13.6 | 850 | 200 | 370 | 100 | 98 |
| 22 | 50 | $5Rh_1RuAl$ | 3 | 2500 | 180 | 45 | 100 | 95 |
| 23 | 50 | $5Rh_1RuAl$ | 3 | 850 | 180 | 150 | 100 | 95 |
| 24 | 50 | $5Rh_1RuAl$ | 1.5 | 850 | 210 | 100 | 100 | 89 |
| 25 | 50 | $5Rh_1RuAl$ | 1.5 | 850 | 185 | 180 | 100 | 95 |
| 26 | 50 | $5Rh_1RuAl$ | 1.5 | 2500 | 185 | 90 | 100 | 95 |
| 27 | 50 | $5Rh_1RuAl$ | 1.5 | 2500 | 190 | 45 | 100 | 95 |
| 28 | 50 | $5Rh_1RuAl$ | 1.5 | 850 | 185 | 60 | 100 | 95 |
| 29 | *50 | $Rh/Al_2O_3$ | 1.5 | 850 | 185 | 100 | 100 | 85 |
| 30 | *50 | $Ru/Al_2O_3$ | 1.5 | 850 | 200 | 315 | 100 | 49 |
| 31 | *50 | $5Rh_1RuAl$ | 1.5 | 850 | 185 | 110 | 100 | 86 |
| 32 | *50 | $5Rh_1RuAl$ | 1.5 | 850 | 185 | 120 | 100 | 87 |
| 33 | *50 | $5Rh_1RuAl$ | 1.5 | 850 | 185 | 145 | 100 | 93 |
| 34 | *50 | $5Rh_1RuAl$ | 1.5 | 1000 | 195 | 175 | 100 | 92 |

| RUN | PCT TT | PCT CT | PCT CC | HEAVIES | SOLVENT | SOL PBV | $NH_3$ PBW | NaOH ML | LiOH MG |
|---|---|---|---|---|---|---|---|---|---|
| 1 | 50 | 40 | 10 | . | THF | 50 | . | 0.4 | . |
| 2 | 50 | 39 | 10 | . | THF | 50 | . | 0.4 | . |
| 3 | 40 | 46 | 14 | . | MeOH | 50 | 3.5 | . | 2.4 |
| 4 | 46 | 54 | 0 | . | MeOH | 50 | . | 0.4 | . |
| 5 | 28 | 50 | 22 | . | MeOH | 50 | 3.5 | . | 2.4 |
| 6 | 30 | 46 | 24 | . | MeOH | 50 | 3.5 | . | 2.4 |
| 7 | 37 | 48 | 15 | . | THF | 75 | . | . | 125 |
| 8 | 9 | 42 | 49 | . | $nBu_2O$ | 50 | . | . | 0 |
| 9 | 7 | 39 | 54 | . | $nBu_2O$ | 50 | . | . | 0 |
| 10 | 10 | 45 | 44 | . | DIOX | 150 | . | . | 500 |
| 11 | 16 | 48 | 36 | . | THF | 50 | . | . | 125 |
| 12 | 12 | 45 | 43 | . | THF | 75 | . | . | 125 |
| 13 | 28 | 49 | 23 | . | DIOX | 100 | . | . | 250 |
| 14 | 26 | 50 | 25 | . | DIOX | 75 | . | . | 250 |
| 15 | 28 | 48 | 24 | . | THF | 75 | . | . | 250 |
| 16 | 16 | 48 | 36 | . | THF | 300 | . | . | 500 |
| 17 | 16 | 47 | 37 | . | THF | 300 | . | . | 500 |
| 18 | 22 | 49 | 29 | . | THF | 300 | . | . | 500 |
| 19 | 17 | 49 | 34 | . | THF | 2000 | . | . | 1440 |
| 20 | 21 | 51 | 29 | . | THF | 1800 | . | . | 1565 |
| 21 | 24 | 50 | 25 | . | THF | 1433 | . | . | 680 |
| 22 | 22 | 49 | 29 | 2.1 | THF | 75 | . | . | 150 |
| 23 | 23 | 50 | 28 | 2.0 | THF | 75 | . | . | 150 |
| 24 | 28 | 50 | 22 | 5.6 | THF | 75 | . | . | 75 |
| 25 | 20 | 50 | 30 | 3.6 | THF | 75 | . | . | 75 |

TABLE 1-continued
METHYLENEDIANILINE HYDROGENATIONS

| 26 | 18 | 48 | 34 | 1.9  | THF | 75 | . | . | 75 |
|----|----|----|----|------|-----|----|---|---|----|
| 27 | 17 | 48 | 34 | 1.5  | THF | 75 | . | . | 0  |
| 28 | 18 | 49 | 33 | 1.8  | THF | 75 | . | . | 0  |
| 29 | 13 | 47 | 40 | 6.8  | THF | 75 | . | . | 0  |
| 30 | 37 | 47 | 15 | 15.2 | THF | 75 | . | . | 0  |
| 31 | 16 | 48 | 36 | 4.1  | THF | 75 | . | . | 0  |
| 32 | 16 | 45 | 39 | 3.7  | THF | 75 | . | . | 75 |
| 33 | 16 | 48 | 35 | 1.2  | THF | 75 | . | . | 0  |
| 34 | 18 | 50 | 32 | 1.4  | THE | 75 | . | . | 0  |

The results in table 1 (Runs 1-7) illustrate the effect of ruthenium catalyst on the conversion of MDA to PACM under a variety of process conditions. The first two runs demonstrate the increased time required for hydrogen uptake to cease as pressure is reduced from 2500 to 850 psi using solely ruthenium. The PACM t/t isomer content is 50% in each case. At 2500 psig ruthenium effects MDA reduction in methanol solvent in the presence of ammonia (run 3), generating 40% t/t isomer. With solely NaOH rather than NH3/LiOH as the alkali moderator the reaction fails at 2500 psig, leading to only 29% conversion and 1% PACM yield. If the same 10% loading of 5% ruthenium on alumina is employed at 850 psi using the NH3/LiOH combination that succeeded at 2500 psig, the GC yield is only 13% after 120 minutes (run 5), 21% after 300 minutes (run 6). Ruthenium moderated by LiOH in THF (run 7) does reduce MDA efficiently at 850 psig within 255 min (run 7), but the t/t isomer is above the desired range at 37%. In summary, excellent conversion and yields may be obtained at high pressures easily with ruthenium, and at lower pressures under more restrictive condition, but in all cases the t/t isomer is high, e.g. above 35% when yields are acceptably high.

Runs 8-12 demonstrate rhodium on alumina reduction of MDA to PACM in n-butyl ether at 5% loading of 5% catalyst and that rhodium was highly effective at 2500 psig, producing 9% t/t isomer in 75 minutes in high yield (run 8). Using the same reagent grade MDA at 850 psig the yield fell to 14% as reaction stopped after 30 minutes. The major product in run 9 was half reduced MDA. Runs 10-12 demonstrate alternative solvent, solvent to substrate ratio and alkali moderation effects. At acceptably high yields the PACM t/t isomer is below the desired range.

Runs 13-21 show the use of rhodium/ruthenium catalyst in first dioxane, then THF as reactors of increasing size were used to generate PACM with 15-30% t/t isomer. From one liter autoclave runs 16-18 the product was distilled. From 634 g crude product obtained after solvent removal following filtration from catalyst, to allow catalyst reuse, a vacuum trap residue (lights) of 0.5%, a forecut of 2.1% (93.2% PACM), heartcut of 90.7 weight percent @99% PACM and a distillation pot residue of 5.4 weight percent were obtained for a mass balance closure of 98.7%. Noteworthy was the low make of higher molecular weight byproducts. In runs 19-21 the solvent:substrate ratio was reduced from 3:1 to 1:1 and the application of catalyst, which was reused from run to run, was reduced to less than 1% of the MDA charge by weight as the PACM t/t isomer content was maintained at 17-24%.

In runs 22-28 the ability of 5:1 rhodium:ruthenium to produce the desired t/t isomer ratio of PACM is demonstrated. "Heavies" are recorded from expanded capillary GC analyses, and indicate the degree of byproduct secondary amine formation. Decreasing hydrogenation pressure from 2500 to 850 psig had no adverse effect other than lengthening reduction time (runs 22 and 23). Lowering application of catalyst but simultaneously increasing temperature to reduce reaction time (run 24) led to higher heavies, lower yield and higher (28%) t/t isomer content. Reducing temperature and allowing longer reaction time at that lower catalyst loading reversed those trends (run 25). At 2500 psig the effect of eliminating LiOH alkali moderation was tested. There was none, as shown for runs 26 and 27. At 850 psig the same ability to run without alkali was confirmed in run 28.

The remaining runs (29-34) were made using a crude methylenedianiline containing 81.6% 4,4'-MDA, 5.3% 2,4'-MDA, 0.1% 2,2'-MDA, 0.3% N-methyl-4,4'-MDA, 0.6% of a three ring analog of MDA (mixture of isomers) and 2.0% of 4 ring and higher oligomers. Rhodium by itself generates 6.8% "heavies" and only 13% t/t isomer in run 29. Also inadequate by itself is ruthenium; the GC yield is but 49% of 37% t/t isomer and the "heavies" are high at 15.2%. The catalyst combining rhodium and ruthenium, used without (run 31) or with (run 32) LiOH alkali promotion, generates acceptably low "heavies" and produces the desired t/t PACM isomer content. In the final runs presented the catalyst is reused, without LiOH addition, to demonstrate low heavies, and, in run 34, 18% t/t PACM.

What is claimed is:

1. A process for the catalytic hydrogenation of crude 4,4,'-methylenedianiline containing from about 10-30% oligomers to a liquid bis-(4-aminocyclohexyl)methane containing from about 17 to 24% by weight of the trans,trans-isomer which comprises hydrogenating said 4,4,'-methylenedianiline in the presence of a mixed metal catalyst system comprising rhodium and ruthenium, the rhodium being present in a weight ratio of from 3 to 7 weight parts rhodium per part ruthenium, based on the weight of the metal component, said hydrogenation being carried out at a temperature of from 170° to 195° C., a hydrogenation pressure of from 700 to 1500 psig, and for a time sufficient to effect hydrogenation of said 4,4,'-methylenedianiline but for a time not to exceed about 300 minutes.

2. The process of claim 2 wherein the rhodium or ruthenium component or both of the catalyst system is carried upon a support.

3. The process of claim 2 wherein at least one of the components of the catalyst system is alkali moderated.

4. The process of claim 3 wherein the support for the catalyst system is alumina, barium sulfate, kieselguhr, carbon, rare earth carbonates, or a rare earth oxide.

5. The process of claim 4 wherein the rhodium component of the catalyst system is alkali moderated prior to effecting said catalyst hydrogenation.

6. The process of claim 3 wherein the alkali moderated catalyst system contains from 0.1 to 15% by weight of a basic metal compound calculated as alkali metal.

7. The process of claim 5 wherein the reaction is carried out in the presence of a solvent.

8. The process of claim 7 wherein said solvent is tetrahydrofuran.

* * * * *